(12) United States Patent
Salemme et al.

(10) Patent No.: US 11,176,727 B2
(45) Date of Patent: Nov. 16, 2021

(54) METHOD AND APPARATUS FOR ACQUIRING A SPATIAL MAP OF AUDITORY PERCEPTION OF A SUBJECT

(71) Applicants: INSTITUT NATIONAL DE LA SANTE ET DE LA RECHERCHE MEDICALE (INSERM), Paris (FR); UNIVERSITÉ CLAUDE BERNARD LYON 1, Villeurbanne (FR); UNIVERSITE JEAN MONNET SAINT ETIENNE, Saint-Etienne (FR); CENTRE NATIONAL DE LA RECHERCHE SCIENTIFIQUE, Paris (FR)

(72) Inventors: Romeo Salemme, Bron (FR); Alessandro Farne, Bron (FR); Valérie Gaveau, Bron (FR); Anaël Belle, Bron (FR); Eric Koun, Bron (FR); Francesco Pavani, Rovereto (IT)

(73) Assignees: INSTITUT NATIONAL DE LA SANTE ET DE LA RECHERCHE MEDICALE (INSERM), Paris (FR); UNIVERSITE CLAUDE BERNARD LYON 1, Villeurbannd (FR); UNIVERSITE JEAN MONNET SAINT ETIENNE, Sainte-Etienne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 170 days.

(21) Appl. No.: 16/303,948

(22) PCT Filed: May 26, 2017

(86) PCT No.: PCT/EP2017/062738
§ 371 (c)(1),
(2) Date: Nov. 21, 2018

(87) PCT Pub. No.: WO2017/203028
PCT Pub. Date: Nov. 30, 2017

(65) Prior Publication Data
US 2020/0320768 A1    Oct. 8, 2020

(30) Foreign Application Priority Data
May 27, 2016 (EP) ..................................... 16305621

(51) Int. Cl.
*G06T 15/00* (2011.01)
*G06T 7/70* (2017.01)
(Continued)

(52) U.S. Cl.
CPC ............ *G06T 15/00* (2013.01); *A61B 5/0077* (2013.01); *A61B 5/1114* (2013.01);
(Continued)

(58) Field of Classification Search
None
See application file for complete search history.

(56) References Cited

U.S. PATENT DOCUMENTS 5,873,735 A * 2/1999 Yamada ............. H04N 1/32112
                                                    235/462.15
9,053,562 B1 * 6/2015 Rabin ................... G06F 16/583
(Continued)

OTHER PUBLICATIONS

Muller et al., "The BoomRoom: Mid-air Direct Interaction with Virtual Sound Sources", CHI 2014, One of a CHInd, Toronto, ON, Canada, 247-256 (Year: 2014).*
(Continued)

*Primary Examiner* — Tapas Mazumder
(74) *Attorney, Agent, or Firm* — W&C IP

(57) ABSTRACT

This method for acquiring a spatial map of auditory perception of a subject comprises a plurality of successive test
(Continued)

sequences, each test sequence comprising steps of: a) calibration (1002) of the subject's position, by displaying instructions to the subject, using a head-mounted visual display system worn by the subject, in order to acquire a reference position of the subject, the subject's position being measured using a video motion capture system by measuring the spatial coordinates of a first optical marker worn by the subject, b) choosing (1004) spatial coordinates of a target location of a sound source, said target cation being located around the subject, c) emitting (1006) a predefined sound, using a sound source placed at said target location, d) in response to acquisition instructions generated by the subject using an acquisition interface, acquiring (1008) an estimated location of said sound source, by using the video motion capture system to measure the spatial coordinates of a second optical marker held and pointed by the subject towards a perceived location of the sound source.

15 Claims, 8 Drawing Sheets

(51) Int. Cl.
| | |
|---|---|
| *A61B 5/16* | (2006.01) |
| *A61B 5/00* | (2006.01) |
| *A61B 5/11* | (2006.01) |
| *A61B 5/12* | (2006.01) |
| *G06F 3/01* | (2006.01) |
| *G06T 7/20* | (2017.01) |
| *H04S 7/00* | (2006.01) |

(52) U.S. Cl.
CPC ............ *A61B 5/1127* (2013.01); *A61B 5/123* (2013.01); *A61B 5/162* (2013.01); *A61B 5/163* (2017.08); *A61B 5/6803* (2013.01); *A61B 5/7475* (2013.01); *G06F 3/013* (2013.01); *G06T 7/20* (2013.01); *G06T 7/70* (2017.01); *H04S 7/30* (2013.01); *A61B 2560/0223* (2013.01); *G06T 2200/24* (2013.01); *G06T 2207/10016* (2013.01); *G06T 2207/30201* (2013.01); *G06T 2207/30204* (2013.01)

(56) References Cited

U.S. PATENT DOCUMENTS

| | | | |
|---|---|---|---|
| 2013/0293688 A1* | 11/2013 | Benson | ............... G02B 27/017 348/53 |
| 2015/0304790 A1 | 10/2015 | Kosei | |
| 2017/0052595 A1* | 2/2017 | Poulos | .................... G06F 3/013 |

OTHER PUBLICATIONS

Mueller et al., "The boomRoom", Human Factors in Computing Systems, Apr. 26, 2014, pp. 247-256.

Zhou et al., "An experimental study on the role of 3D sound in augmented reality environment", Interacting With Computers, Butterworth-Heinemann, GB, vol. 16, No. 6, Dec. 1, 2004, pp. 1043-1068.

Seeber B U et al., "A system to simulate and reproduce audiovisual environments for spatial hearing research", Hearing Research, Elsevier Science Publishers, Amsterdam, NL, vol. 260, No. 1-2, Feb. 1, 2010, pp. 1-10.

Schwarze et al., "A Camera-Based Mobility Aid for Visually Impaired People", Ki. Kuenstliche Intelligenz, Arendtap Desktop Publishing, Bremen, DE, vol. 30, No. 1, Oct. 15, 2015, pp. 29-36.

Lewald et al., "The effect of gaze eccentricity on perceived sound direction and its relation to visual localization", Hearing Research, vol. 115, No. 1-2, Jan. 1, 1998, pp. 206-216.

Brungart et al., "Auditory localization of nearby sources.II. Localization of a broadband source", J. Acoust. Soc. Am. 106 (4), Pt. 1, Oct. 1999, pp. 1956-1967.

\* cited by examiner

METHOD AND APPARATUS FOR ACQUIRING A SPATIAL MAP OF AUDITORY PERCEPTION OF A SUBJECT

TECHNICAL FIELD OF THE INVENTION

The invention relates to a method for acquiring a spatial map of auditory perception of a subject and an apparatus for acquiring said spatial map.

BACKGROUND OF THE INVENTION

Methods are known for measuring the auditory ability of a subject, for example to detect auditory perception impairments of a subject or for performing reeducation on subjects who have been received hearing aids or implantable hearing devices.

An example of one such method is described in the article by DOUGLAS S BRUNGART et al. "Auditory Localization of Nearby Sources. Localization of a Broadband Source", Journal of the Acoustical Society of America, 106(4), October 1999, pp.1956-1968.

In this method, a subject is seated in a fixed position with his head restrained on a chin rest. An operator moves a sound source around, at various successive locations around the subject. The subject responds to the sound by pointing towards an estimated position of the sound source, without seeing the sound source, here using a rod held in a free hand and equipped with a position sensor. Another position sensor is held by the operator with the sound source. A tracking system, connected to a control unit, monitors the position of both position sensors, relatively to the subject's head. A comparison can be drawn between the estimated and actual positions.

This known method is not entirely satisfactory. One of its drawbacks is that the subject must be constrained and cannot move during the entire test. This is highly uncomfortable and can impair the ability of the subject to concentrate, reducing the effectiveness of the method. Furthermore, this setting does not correspond to the typical behaviour of the subject in everyday contexts, further reducing the effectiveness of the method. This is especially problematic when the method is used on children. Another drawback is that the sound source is moved at successive arbitrary locations determined by a human operator. This introduces uncontrolled uncertainty as to where sounds are presented, makes comparison across subjects or test-re-test within the same subject not possible, and ultimately does not allow a standardized mapping of spatial hearing. In addition, there is a risk that successive positions follow a predictable pattern. If the subject perceives this pattern, even unconsciously, he may cheat and rely on this knowledge to locate the sound source, instead of relying only on his auditory system. The precision and effectiveness of the method is therefore reduced.

SUMMARY OF THE INVENTION

An object of the present invention is therefore to provide a method for acquiring a map of auditory perception of a subject, in which data can be collected more efficiently and with an improved precision, while at same time providing a more comfortable setting for the subject.

To that end, the invention relates to a method for acquiring a spatial map of auditory perception of a subject, wherein said method comprises a plurality of successive test sequences, each test sequence comprising steps of:

a) calibration of the subject's position, by displaying instructions to the subject, using a head-mounted visual display system worn by the subject, in order to acquire a reference position of the subject, the subject's position being measured using a motion capture system by measuring the spatial coordinates of a first location marker worn by the subject, this head-mounted display system preventing the subject from seeing his surroundings;

b) choosing spatial coordinates of a target location of a sound source, said target location being located around the subject, c) emitting a predefined sound, using a sound source placed at said target location, d) in response to acquisition instructions generated by the subject using an acquisition interface, acquiring an estimated location of said sound source, by using the motion capture system to measure the spatial coordinates of a second location marker held and pointed by the subject towards a perceived location of the sound source and measuring an orientation of the subject's gaze, using an eye-tracking device integrated with the head-mounted visual display system.

According to the invention, the target location of each test sequence is different from the target location of, at least, the previous test sequence.

Thanks to the invention, the measurement of the perceived location is improved. Additionally, the head mounted display system allows a greater freedom of movement for the subjects and allows accurate positioning of the subject even in case of unrestrained movement of the head. Furthermore, it facilitates a smoother implementation of the calibration step, by displaying visual instructions to the subject and how to align his head and eyes in a desired position. This way, precise visual instructions can be provided to the subject while at the same time preventing the subject from seeing the test room in which the apparatus is located. For this reason, it is not possible to use a video screen to display such instructions, because the subject would then see its immediate environment including a sound source, which could give him visual clues and reduce the effectiveness of the method.

According to advantageous aspects, the invention comprises one or more of the following features, considered alone or according to all possible technical combinations:

The target location of each test sequence is different from the target location of, at least, the previous test sequence.

The method further comprises an automatic computation of a difference between each estimated location and each corresponding target location.

Step d) further comprises the measurement of an orientation of the subject's head, by measuring the spatial coordinates of the first location marker using the motion capture system relative to a fixed position.

The motion capture system is a video motion capture system and the first and second markers are optical markers.

Step a) comprises displaying positioning instructions on the head-mounted visual display.

During step b), the target location is selected randomly.

Step b) further comprises:
displaying the spatial coordinates of the target location, and determining the actual position of the sound source, using the motion capture system to measure spatial coordinates of a third location marker placed on the sound source.

The third location marker is an optical marker.

The method further comprises generating a graphical representation of said acquired estimated locations of the sound source.

Said graphical representation is three-dimensional graphical representation displayed on a graphical user interface.

According to another aspect, the invention relates to an apparatus for acquiring a spatial map of auditory perception of a subject, wherein said apparatus comprises:

a head-mounted visual display system, adapted to be worn by a subject and configured for displaying instructions to the subject, this head-mounted display system preventing the subject from seeing his surroundings, the head-mounted visual display system further comprising an eye-tracking device;

a motion capture system, a first location marker and a second location marker, the motion capture system being configured for measuring the spatial coordinates of said first and second location markers, a sound source, configured for being placed at a target location around the subject, an acquisition interface, configured for being commanded by the subject, wherein said apparatus further comprises a control unit programmed to implement a plurality of successive test sequences, each test sequence comprising steps of:

a) calibration of the subject's position, by displaying instructions to the subject, using the head-mounted visual display system worn by the subject, in order to acquire a reference position of the subject, the subject's position being measured using the motion capture system by measuring the spatial coordinates of the first location marker, said first location marker being worn by the subject, b) choice of spatial coordinates of a target location of the sound source, said target location being located around the subject, c) emission of a predefined sound, using said sound source placed at said target location, d) in response to acquisition instructions generated by the subject using the acquisition interface, acquisition of an estimated location of said sound source using the motion capture system by measuring the spatial coordinates of the second location marker, said second location marker being held and pointed by the subject towards a perceived location of the sound source and a step of measurement of an orientation of the subject's gaze using the eye-tracking device.

The control unit is further programmed, during step b), to choose spatial coordinates of a target location that is different from the target location of, at least, the previous test sequence.

According to advantageous aspects, the invention comprises one or more of the following features, considered alone or according to all possible technical combinations:

The control unit is further programmed to compute automatically a difference between each estimated location and each corresponding target location.

The motion capture system is a video motion capture system and the first and second markers are optical markers.

BRIEF DESCRIPTION OF THE DRAWINGS

The invention will be better understood upon reading the following description, provided solely as an example, and made in reference to the appended drawings, in which.

DETAILED DESCRIPTION OF SOME EMBODIMENTS

Figure 1:
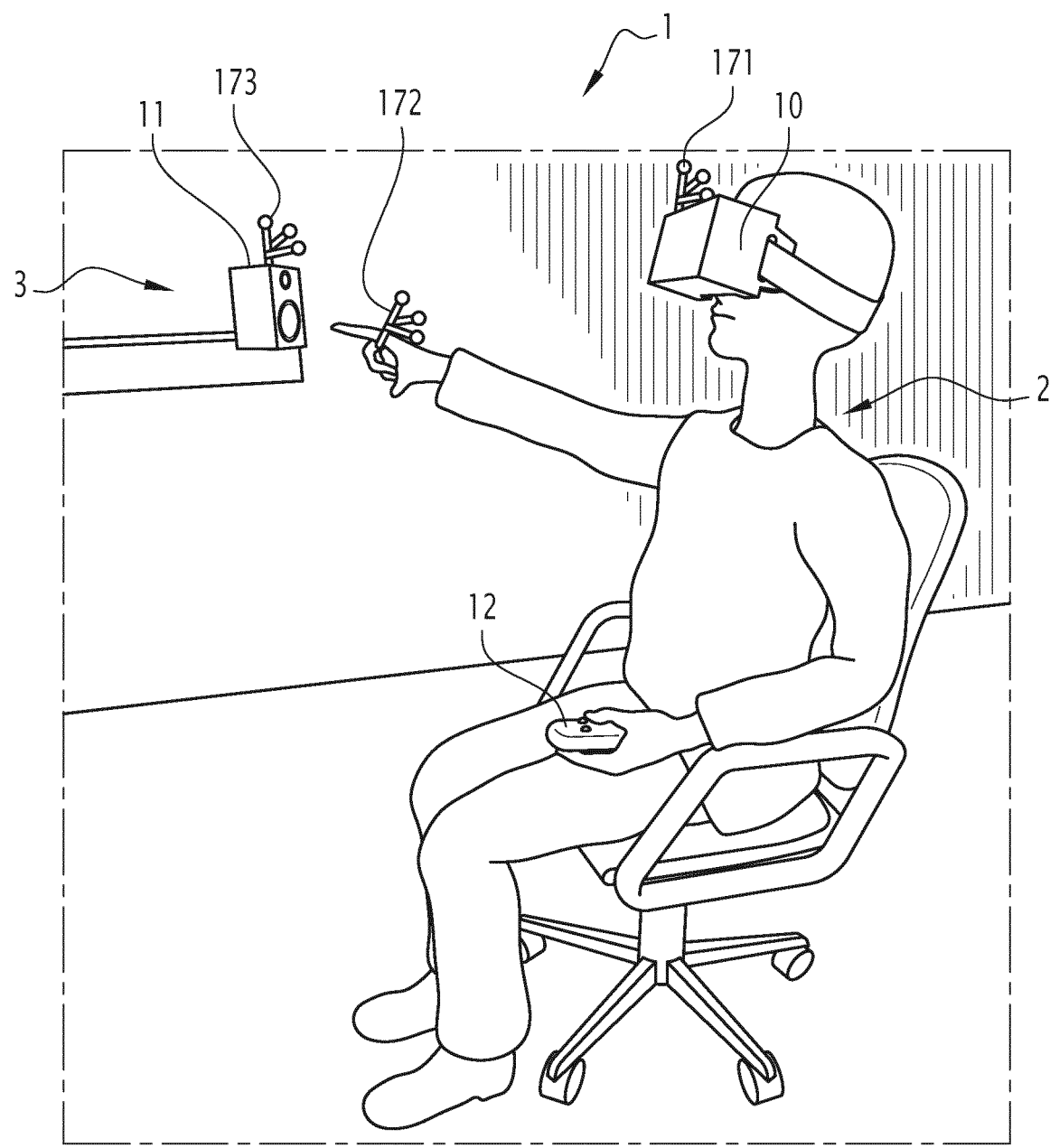
FIG. 1 is a simplified illustration of an experimental setup for acquiring a spatial map of auditory perception of a subject, including an apparatus for acquiring a spatial map of auditory perception according to the invention.

FIG. 1 represents an experimental setup, comprising an apparatus 1 for acquiring a spatial map of auditory perception of a human subject or patient 2. Part of apparatus 1 and subject 2 are located in a testing room 3.

Subject 2 has a head 20 and a hand 22. Head 20 defines a geometrical center 21, and is provided with ears 23 and eyes. Subject 2 is not part of apparatus 1. In a working configuration of apparatus 1, subject 2 is seated at a predefined position inside room 3.

Apparatus 1 comprises a head-mounted visual display system 10, a movable sound source 11, an acquisition interface 12, a programmable control unit 13 and a motion capture system 14. In this example, apparatus 2 also comprises a first marker 171, a second marker 172 and a third marker 173. Apparatus 1 further comprises a visual instructions monitor 18 whose role is described in what follows.

In this exemplary embodiment, the motion capture system 14 is a video motion capture system and the location markers 171, 172 and 173 are optical markers.

However, in other embodiments, other motion capture technologies may be used instead of optical-based technologies. For example, the motion capture system 14 may be based on movement sensors, such as accelerometers and/or gyroscopes, which measure a movement in space, the location being then calculated using said measured movement. In alternative embodiments, the motion capture system 14 may be adapted to detect magnetic location markers. In still other embodiments, motion capture system 14 may use a combination of technologies, e.g. optical and magnetical, to detect and measure the location of said location markers.

In any case, the location markers are modified accordingly, so as to be compatible with motion capture system 14, i.e. to that motion capture system 14 may measure their respective locations in space.

In such embodiments, everything that is disclosed in reference to the remainder of system 1 also applies, regardless of the technology used by the motion capture system.

Head-mounted display 10 is adapted to be worn by subject 2, on his/her head 20.

Head-mounted display system 10 comprises video screens adapted to be positioned facing the eyes of subject 2 when worn. When head-mounted display 10 is worn on head 20, subject 2 cannot see its surroundings in testing room 3. In other words, the subject 2 is prevented from seeing its surroundings. Head-mounted display 10 obstructs the field of view of the subject 2 when worn. For example, head-mounted display 10 comprises a portion made of an opaque material which obstructs the field of view of subject 2 when worn. This allows for full control over the visual information provided during the test. Visual information can include experimental instructions, instructions for the user's posture (e.g., straight ahead, or desired eye position), information about the overall structure of the real or fictitious environment, information about the exact or fictitious location of sound sources, or any other visual feedback that may be useful to measure or improve sound localization performance. For example, head mounted display 10 is an OCULUS RIFT® virtual reality headset. Head-mounted display system 10 is connected to control unit 13 through a video interface 132.

Optionally, head-mounted display 10 is adapted to allow an operator of apparatus 1 to selectively display the location of sound source 11 to subject 2 or to display specifically chosen visual cues. This way, specific abilities of subject 2 may be tested, because the ability to localize sounds is known to be influenced by available cues. This allows a greater freedom of experimentation for the operator of apparatus 1.

Preferably, head-mounted display 10 comprises an eye tracking device, not illustrated, configured for measuring an orientation of the gaze of the subject 2 when head-mounted display 10 is worn. For example, the eye tracking device is the apparatus sold by SMIVISION of Teltow, Germany, under the commercial reference "Eye Tracking Oculus Rift®".

Sound source 11 is configured for emitting a predefined sound upon receiving a command from control unit 14. Sound source 11 is movable within room 3 around subject 2 and is able to be placed at several target positions, as explained in what follows. For example, sound source 11 is a loudspeaker or a buzzer.

Acquisition interface 12 is configured for being controlled by subject 2 and comprises to this end a touch key to be pressed by subject 2. When this key is pressed, interface 12 transmits an acquisition signal to control unit 14. For example, interface 12 is a remote control.

Control unit 13 is programmed to operate head-mounted display 10, sound source 11 and motion capture system 14. Control unit 13 is also programmed to receive acquisition signals from acquisition interface 12. Control unit 13 comprises a data processing unit, a data storage unit and an external communication interface. For example, control unit 13 includes a personal computer 131 which incorporates said data processing unit and said data storage unit.

Said data processing unit comprises a microprocessor or a programmable microcontroller. Said data storage unit comprises a Flash memory module, a hard disc drive or an EEPROM memory module. Data storage unit contains instructions executable by data processing unit in order to execute one or several successive test sequences for acquiring a spatial map of auditory perception of subject 2, using the method of FIG. 6. Said interface comprises a serial communication port, a USB port or an electrical connector such as a RF connector. Said interface may also be a wireless communication interface. Said data storage unit and data processing unit are linked together and to said interface by a data communication bus.

Preferably, control unit 13 is located outside of room 3, in order not to disturb subject 2.

Figure 2:
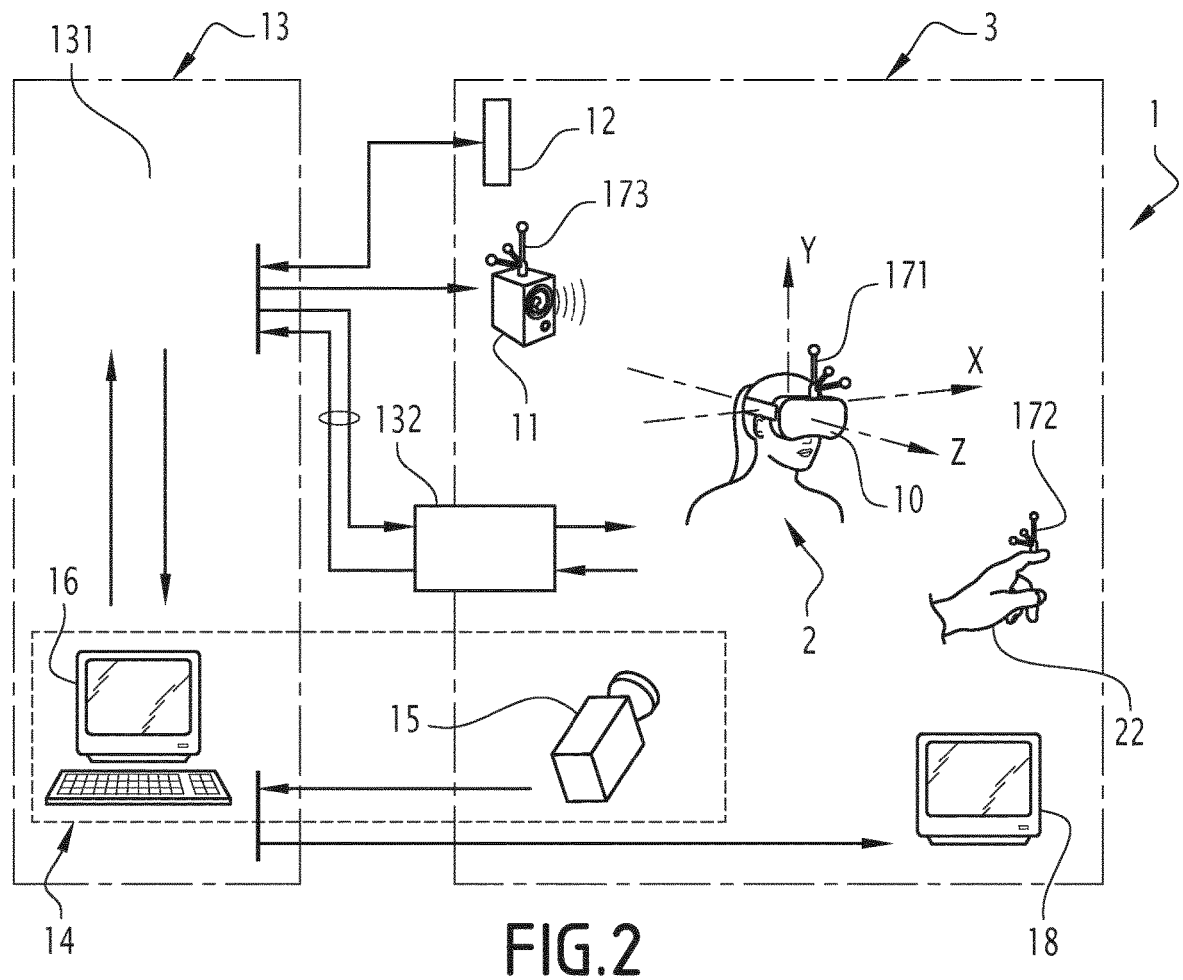
FIG. 2 is a diagrammatic representation of the apparatus of FIG. 1.

Motion capture system 14 is configured for measuring the spatial coordinates of optical markers 171, 172 and 173. Advantageously, motion capture system 14 is able to track the position of optical markers 171, 172 and 173 in real time. To this end, motion capture system 14 comprises a set of cameras 15 and a control module 16 connected to cameras 15. Here, control module 14 is part of control unit 13. On FIG. 2, only one camera 15 is represented for the sake of simplicity, but motion system capture 14 preferably includes several cameras, which improves its accuracy. Said cameras 15 are not visible on FIG. 1.

As is known, cameras 15 are able to detect optical markers 171, 172 and 173. In this embodiment, cameras 15 are infrared cameras and comprise each an infrared light source. Optical markers 171, 172 and 173 each comprise an external surface comprising a reflective material, which reflects infra-red light emitted by the light source towards cameras 15, thus allowing detection of optical markers 171, 172 and 173 and computation of their respective spatial coordinates by control unit 13, relative to center 21. For example, motion capture system 14 is the "BONITA®" motion capture system sold by VICON MOTION SYSTEMS LTD of Oxford, United Kingdom.

As explained above, the motion capture system 14 may be different. In that case, the optical markers 171, 172 and 173 are replaced by location markers which are not necessarily based on optical recognition and which are compatible with motion capture system 14. Yet, what is described in reference to the location and the role of markers 171, 172 and 173 described herein can be transposed to non-optical location markers.

In this example, first optical marker 171 is placed on head-mounted display 10, in order to measure the position of subject 2 and the orientation of head 20. Second optical marker 172 is adapted to be held by subject 2 in his/her hand 22. Optical marker 172 is meant to measure spatial coordinates of an estimated location of sound source 11 as perceived by subject 2 during each test sequence, as explained in what follows. The third optical marker 173 is placed on sound source 11, in order to measure the actual position of sound source 11.

In another embodiment, optical marker 172 is placed on acquisition interface 12, possibly integrated within said acquisition interface 12. Therefore, subject 2 need only use one hand during the test, which is more comfortable.

Cameras 15 are placed in room 3, for example spread around subject 2 and pointed towards subject 2, so that subject 2 is included in their respective fields of view in a working configuration of apparatus 1.

As an illustrative example, motion capture system 14 comprises seven cameras 15, arranged along a circle centered on center 21 above subject 2. The number of cameras 15 can however be different and may be adapted depending on several environmental parameters, such as the spatial configuration and/or the lighting conditions of room 3 and/or the features of motion capture system 14.

In this embodiment, spatial coordinates are expressed in an orthogonal Cartesian reference system, centered on center 21 of head 20. Said reference system comprises three orthogonal geometrical axes X, Y and Z. Axis Y is arranged vertically. The geometrical plane comprising axes Y and Z, noted plane YZ, forms a sagittal plane of subject's head 20. The geometrical plane comprising axes X and Z, noted plane XZ, forms a transverse plane of head 20. Axes X, Y and Z are immobile relatively to head 20.

In this description, the orientation D of head 20 is defined as a vector originating from center 21 and passing through a point, named "cyclopean eye", located at middle distance between the respective geometrical centers of the eyes of subject 2. The gaze orientation of subject 2 is defined as a vector originating from said cyclopean eye and passing through the focalization point of the subject's eyes. In this embodiment, orientation D is permanently aligned with axis Z.

A fixed reference system comprising three orthogonal axes $X_0$, $Y_0$ and $Z_0$ is defined as anchored to room 3. For example, during a pre-calibration phase, said axes $X_0$, $Y_0$ and $Z_0$ are defined as being equal to axes X, Y and Z, respectively when subject 2 is in the predefined position or is in an arbitrary initial position. When subject 2 later changes his/her position, axes X, Y and Z move along with his/her head and axis $X_0$, $Y_0$ and $Z_0$ remain fixed to room 3.

In a so-called predefined reference position of subject 2, head 20 is standing vertically along axis Y with the eyes of subject 2 looking straight ahead. Orientation D is then comprised in plane YZ and is aligned with axis $Z_0$. As an illustrative example, head orientation D is said to be aligned with axis $Z_0$ if the angle between orientation D and axis $Z_0$ is smaller than 5°, preferably smaller than 2°. This angle is known thanks to the position of optical marker 171. Of course, such predefined position is not mandatory. Preferably, in the so-called reference position of subject 2, the gaze orientation of subject 2 is aligned with head orientation D.

Figure 3:
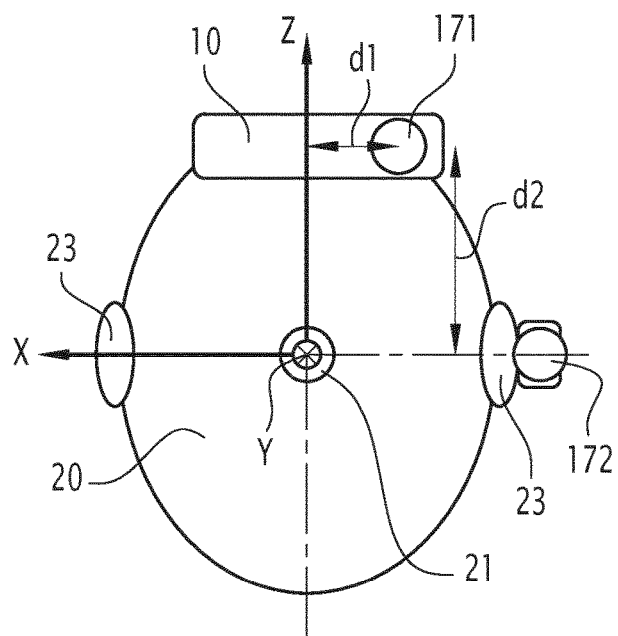
FIG. 3 and FIG. 4 are schematic illustrations of a reference system for spatial coordinates defined relative to a head of the subject of the setup of FIG. 1.
Figure 4:
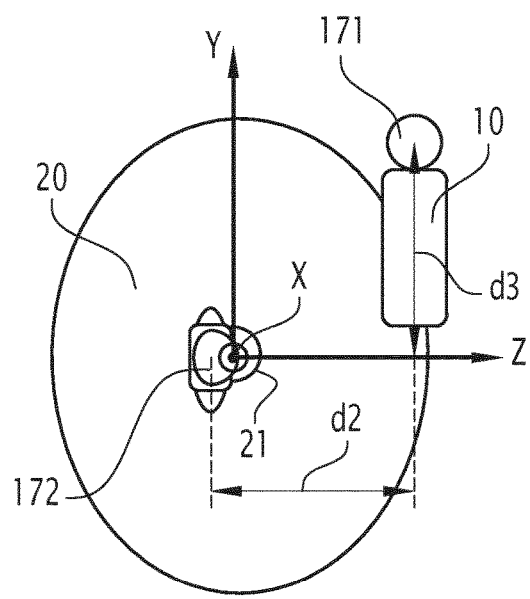

FIGS. 3 and 4 illustrate the position of head-mounted display 10 relative to head 20 during pre-calibration phase. In this pre-calibration phase, subject 2 is asked to place optical marker 172 against one of its ears 23, for example his right ear 23. Alternatively, optical marker 172 is placed by an operator of apparatus 1.

Distance "d1" is defined in plane XZ as the shortest distance between plane YZ and the orthogonal projection in plane XZ of the geometrical center of optical marker 171. For example, d1 is fixed equal to 5 cm.

Distance "d2" is defined as the distance, measured along axis Z, between the geometrical projections in plane XZ of the centers of optical markers 171 and 172.

Distance "d3" is defined as the distance, measured along axis Y, between plane XZ and the geometrical projection in plane YZ of the center of marker 171. For simplification purposes, each optical marker is modeled as a sphere of radius equal to 6 mm.

Therefore, spatial coordinates of center 21 can be computed by control unit 13 from the known positions of optical markers 171 and 172. For example, the spatial coordinates of center 21 are computed as follows:

x_head=x_calib−(x_calib−x_hmd)−d1
y_head=y_hmd−d3
z_head=z_hmd−d2 where:
"x_head", "y_head" and "z_head" are the spatial coordinates, along axis X, Y and Z respectively, of center 21,
"x_hmd", "y_hmd" and "z_hmd" are the spatial coordinates, along axis X, Y and Z respectively, of optical marker 171 mounted on head-mounted display 10, and
"x_calib" is the spatial coordinate, along axis X, of optical marker 172 held by subject 2 against its right ear 23 during calibration phase.

In another embodiment, in this pre-calibration phase, the optical marker 172 is placed successively against each of the subject's ears 23 in order to acquire the spatial coordinates of both ears 23. Once the coordinates of both ears are known, a so-called interaural axis is defined, as a segment of line connecting both ears 23, i.e. connecting the respective geometrical centers of the optical marker 172 in its successive positions against each ear 23. Center 21 is then defined as being located at the middle of the interaural axis.

Figure 5:
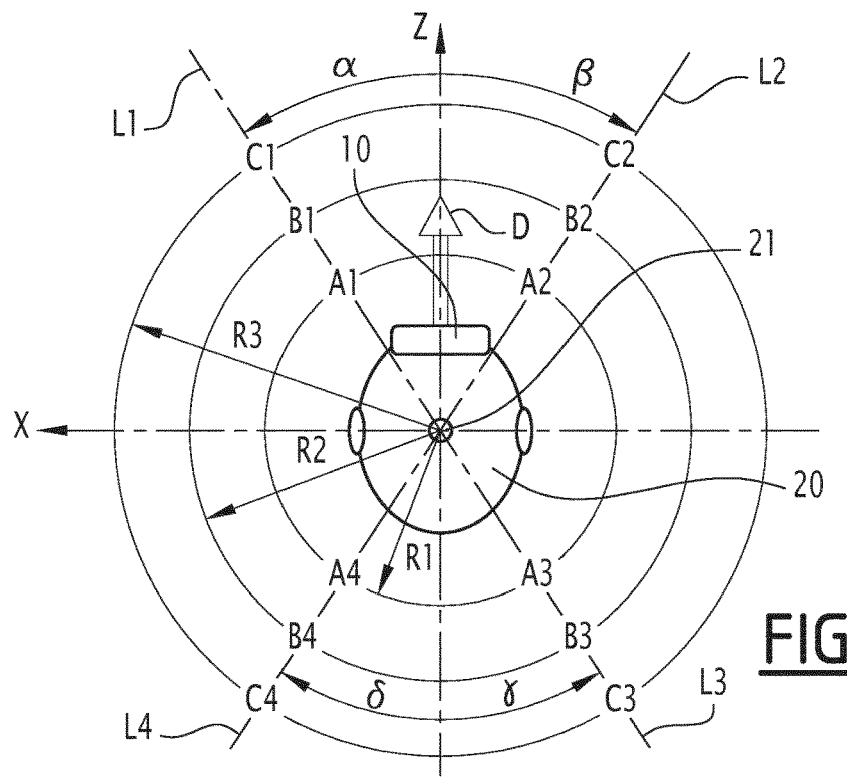
FIG. 5 illustrates schematically predefined target locations for placing a sound source of the apparatus of FIG. 1.

FIG. 5 illustrates predefined target locations on which sound source 11 is meant to be placed. In this example, said target locations are located in plane XZ and are spread between three concentric circles centered on center 21 and having respective radii R1, R2 and R3. For example, R1 is equal to 25 mm, R2 is equal to 45 mm and R3 is equal to 65 mm.

In this illustrative example, twelve target locations are predefined. Predefined target locations of the first circle of radius R1 are named A1, A2, A3, and A4. Similarly, predefined target locations of the second circle of radius R2 are named B1, B2, B3, and B4 and predefined target locations of the third circle of radius R3 are named C1, C2, C3, and C4.

Here, said locations are further located at the intersection of said three circles and four straight lines belonging to plane YZ and passing through center 21. Locations A1, B1 and C1 are aligned on a first line L1 on a forward side of head 20, said first line L1 having an angle α of 30° relative to plane YZ. Locations A2, B2 and C2 are aligned on a second line L2 on a forward side of head 20, said second line L2 having an angle β of 30° relative to plane YZ, opposite to locations A1, B1 and C1. Similarly, locations A3, B3 and C3 are aligned on a third line L3 on a rear side of head 20, said third line L3 having an angle γ of 30° relative to plane YZ, and are arranged symmetrically to locations A2, B2 and C2 relative to a geometrical plane XY comprising axis X and Y. Locations A4, B4 and C4 are aligned on a fourth line L4 on a rear side of head 20, said fourth line L4 having an angle δ of 30° relative to plane YZ, symmetrically to locations A3, B3 and C3 relative to plane YZ.

In this description, the forward side of head 20 denotes the side of head 20 comprising the eyes of subject 2. The rear side denotes the side of head 20 opposite to the forward side.

The spatial coordinates of said predefined locations are recorded in data storage unit of control unit 13, and are expressed relatively to center 21. Once spatial coordinates of center 21 are known, thanks to the initial calibration phase as described above, said coordinates can be computed as absolute coordinates relative to a coordinate system fixed relative to center 1.

Control unit 13 is programmed to choose automatically a target location for each test sequence, so that, the target location of each test sequence is preferably different from the target location of, at least, the previous test sequence. Alternatively, this is not necessarily the case and target locations may be repeated from one test sequence to another.

For example, the method for acquiring a spatial map of auditory perception of subject 2 comprises a succession of individual test sequences similar to each other. Here, the test is divided into two parts. During a first part, the subject is meant to keep his head 20 in the reference position, that is to say with orientation D aligned along axis Z. In a second part, subject 2 is free to move his head. The first and second parts comprise the same number of test sequences. The test sequences can however be arranged differently, for example by mixing sub-sequences where subject 2 must keep head 20 aligned, with sub-sequences where subject 2 is allowed to move head 20.

In this example, the method comprises a succession of 192 identical test sequences. Therefore, each one of the twelve predefined target locations A1, B1, C1, A2, B2, C2, A3, B3, C3, A4, B4 and C4 is used sixteen times during the whole test.

For each test sequence, each target location is chosen randomly by control unit 14 among the list of predefined target locations A1, B1, C1, A2, B2, C2, A3, B3, C3, A4, B4 and C4, for example by means of a random or pseudo-random number generator.

This arrangement prevents subject 2 from learning the order in which the target locations are chosen for each sequence. The invention solves the problem of how to place the sound source without using a predefined pattern that is easy for the subject to predict.

According to another alternative embodiment, the spatial coordinates of the target location is chosen randomly for each test sequence. In this case, target test locations A1, B1, C1, A2, B2, C2, A3, B3, C3, A4, B4 and C4 are not predefined. However, the only constraint is that the chosen target location must preferably be at arm's length of subject 2 so that subject 2 can point the perceived position of sound source 11 using optical marker 172 held in his arm 21.

Alternatively, the number of predefined target locations may be different. Said target locations are not necessarily comprised inside plane XZ and may be placed at different heights along axis Y.

In this example, sound source 11 is meant to be placed by hand by an operator of apparatus 1. To this end, control unit 13 is further programmed to assist said operator by measuring the actual position of sound source 11 using motion capture system 14 thanks to the third optical marker 173, and comparing it, in real time, to the chosen target location. Control unit 13 further computes the difference between actual position and predefined location, if any, and displays it on monitor 18, allowing the operator to place sound source 11 with a greater precision.

Sound source 11 is said to be successfully placed at the selected target location if the geometrical center of said sound source 11 belongs into a sphere of predefined diameter, for example 6 cm, centered on the spatial coordinates of the chosen target location.

Said difference can be displayed differently to said operator, for example acoustically. In this case, the operator wears audio headphones connected to control unit 13. The headphones generate a sound indicating whether sound source 11 is at the selected target location or not, for example by varying the intensity and/or frequency of the sound whenever the position of sound source 11 approaches the selected target location. Such headphones may be used along instructions monitor 18 or may replace it altogether.

In an alternative embodiment, sound source 11 is placed automatically at the target location, by control unit 13. For example, apparatus 1 comprises a robotic mechanical arm comprising several segments linked together and movable relative to each other using actuators commanded by control unit 13. The sound source 11 may also be placed on a motorized support automatically movable between the predefined target locations along one or several fixed guiding rails.

In another alternative embodiment, apparatus 1 comprises several sound sources 11, placed at various locations in room 3. Each predefined target location corresponds to a position of one of said sound sources 11. However, with such an embodiment, subject 2 may see the position of sound sources 11 when he enters room 3.

Third marker 173 may be omitted if one is certain that the sound source 11 will be placed at selected target locations with good accuracy, for example when sound source 11 is moved using the above-mentioned mechanical means.

Figure 6:
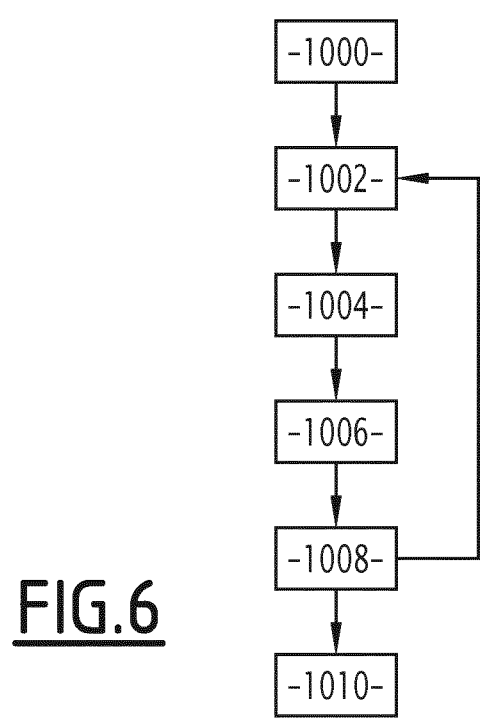
FIG. 6 is a flow diagram of a method for acquiring a spatial map of auditory perception of a subject, using the apparatus of FIG. 1.

An embodiment of a method for acquiring a spatial map of subject 2 using apparatus 1 is now described, with reference to the flow diagram of FIG. 6.

Initially, during a pre-calibration step 1000, subject 2 is placed in room 3 equipped with apparatus 1. For example, subject 2 is seated in a chair located in a predefined location of room 3 towards which cameras 15 are pointed.

First, subject 2 is placed in the reference position, for example by instructing subject 2, to place his head 20 straight. This can be done using visual aids displayed on the display screens of head-mounted display 10, by displaying two graphical symbols, one of them being fixed in place and the other moving along head 20. Both symbols are superposed with each other when head 20 is in the desired position. This way, it is easier for subject 2 to know how his/her head 20 is positioned in space. However, it is not necessary to place subject 2 in such a position. Instead, the subject 2 may be in any position, since axes X, Y and Z are anchored to head 20. Said visual aids may remain present during the subsequent test sequences, so as to prevent any unwanted movement of head 20.

Then, in a sub-step of pre-calibration step 1000, optical marker 172 is placed in a predefined position next to head 20, here along both ears 23. The respective spatial coordinates of markers 171 and 172 are automatically measured by motion capture system 14 and forwarded to control unit 13. The coordinates of center 21 are then computed by control unit 13.

Advantageously, during pre-calibration step 1000, the orientation of the eyes of subject 2 is measured using the eye-tracking device of head-mounted display 10 and subject 2 is instructed to look straight ahead, so that his/her gaze is aligned with head orientation D.

This is done using different visual aids displayed on the display screens of head-mounted display 10, by displaying two graphical symbols, one of them being fixed in space and the other, here in the shape of a sphere, moving along the eyes of subject 20. Both symbols are superposed with each other when said eyes are in the desired position. This way, it is easier for subject 2 to position his eyes with the right gaze orientation. Said visual aids may remain present during the subsequent test sequences, so as to prevent any unwanted movement of the eyes.

At the end of this pre-calibration step 1000, subject 2 is in the predefined reference position, with head orientation D is aligned with axis Z and his gaze orientation aligned with head orientation D.

Once pre-calibration step 1000 is over, control unit 13 initiates a plurality of successive individual test sequences similar to each other. A first test sequence unfolds as follows.

First, during a calibration step 1002, the position of subject 2 is calibrated, by acquiring a reference position of subject 2. More precisely, instructions are displayed to subject 2 using head-mounted display 10 in order to place or replace subject 2 into the predefined reference position. The position of subject 2 and head orientation D are measured, by using motion capture system 14 to measure the spatial coordinates of optical marker 171. If said measured position of subject 2 is different from the reference position of step 1000, subject 2 is instructed to return to the reference position by displaying instructions to subject 2 using head-mounted device 10, in the same way as described in reference to step 1000, for example by using said visual aids. At this stage, it is not necessary however to repeat the pre-calibration step and for the subject to move optical marker 172 to its ear 23. Alternatively, subject 2 is not necessarily replaced in the predefined position. Instead, a fixed position is defined from his/her current position and any further change of head orientation D is measured against the difference between axis Z, which is fixed to head 20, and axis $Z_0$ of said fixed position.

Preferably, the gaze direction of subject 2 is also measured and subject is also instructed to return to return his/her gaze to the reference position, in the same way as described in reference to pre-calibration step 1000.

At the end of step 1002, subject 2 has returned to the predefined reference position.

Then, during a step 1004, control unit 13 automatically selects spatial coordinates of a target location for sound source 11. In this embodiment, control unit 13 selects randomly a target location among the list of predefined target locations A1, B1, C1, A2, B2, C2, A3, B3, C3, A4, B4 and C4 and determines the corresponding spatial coordinates of said chosen target location. For example, predefined target location A1 is chosen.

In this embodiment, there is only one sound source 11, which must be moved to the chosen target location, for example by an operator. Control unit 13 displays instructions, here on instructions monitor 18, so as to indicate to the operator where the sound source 11 must be placed. For example, this is done by displaying a schematic graphical representation similar to the one of FIG. 5 in which the selected target location is highlighted.

The actual position of sound source 11 is determined by motion capture system 14 thanks to the third optical marker 173, and compared in real time to the chosen target location. The difference between actual position and predefined location, if any, is computed by control unit 13 and displayed on monitor 18, allowing the operator to place sound source 11 with a greater precision. This real time measurement, as well as displaying instructions on instructions monitor 18, may be omitted when one is sure that sound source 11 is placed at the chosen target locations with good accuracy, for example when sound source 11 is moved automatically instead of being moved by an operator of apparatus 1.

Once sound source 11 is located at the chosen target location as a result of step 1004, then, control unit 13 commands, during a step 1006, the emission of a predefined sound from sound source 11. For example, a signal is sent by control unit 13 to sound source 11 to play a predefined sound, such a buzzing noise. Said predefined sound is shorter than 5 seconds, preferably shorter than 1 second although the method does not mandate any specific limit of the sound duration.

Subject 2 then hears this emitted sound using his/her auditory system and determines the perceived location of sound source 11 without seeing sound source 11. Subject 2 indicates said perceived location by holding optical marker 172 and pointing it towards the perceived location of sound source 11, preferably by placing it at the point in space around him/her that he/she assumes to be the source of the emitted sound. Once this optical marker 172 is placed, subject 2 activates the acquisition interface 12 by pressing the touch key. Acquisition instructions are then generated by acquisition interface 12 and forwarded to control unit 13. This is the end of step 1006.

Alternatively, subject 2 may be selectively shown visual clues indicating the location of sound source 11, thanks to head mounted on display 10, depending on the needs of the operator of apparatus 1.

Then, during a further step 1008, in response to the acquisition instructions, the estimated location of sound source 11 is acquired, by using video motion capture system 14 to measure the spatial coordinates of optical marker 172. Said measured spatial coordinates are then recorded by control unit 13.

In this embodiment, during this step 1008, the orientation of the gaze of subject 2 is also measured by the eye-tracking device integrated with head-mounted visual display system 10 and is recorded by control unit 13. This feature is advantageous, as it makes possible to detect interactions between the auditory system and the visual system of subject 2.

Optionally, this step 1008 further comprises the measurement of an the orientation D of the subject's head, by measuring the spatial coordinates of the first optical marker 171, relative to a reference position, for example using motion capture system 14.

At the end of this test sequence, control unit 13 holds records of the spatial coordinates of the estimated and actual positions of sound source 11. Subsequent test sequences are then performed successively, one after the other, by repeating steps 1002, 1004, 1006 and 1008 for each test sequence. More specifically, during each step 1004, the chosen target location is different from the target location of, at least, the previous test sequence.

Said steps 1002, 1004, 1006 and 1008 are repeated a predefined number of times. At the end of said test sequences, control unit 13 holds records of the spatial coordinates of the estimated and actual positions of sound source 11 for every test sequence, for several distinct locations of sound source 11. Said spatial coordinates form a spatial map of auditory perception of subject 2. This way, the auditory perception capabilities of subject 2 are measured for different regions of space around subject 2.

Thanks to apparatus 1, the acquisition of the estimated location of sound source 11 is more reliable than known systems of the state of the art, due to the fact that it is possible to measure sound location in free-field space, without constraining subject 2. Additionally, head mounted display 10 allows a greater freedom of movement, as subject 2 does not need to be restrained physically during the entire test. The method is thus more comfortable and more active to typical behaviour of subject 2 in everyday contexts. It is also less stressful for subject 2, especially for younger children. Steps 1000 and 1002 are easier to implement, while preventing subject 2 from seeing room 3 in which apparatus 1 is located.

Optionally, the method further comprises the generation of a graphical representation of said acquired estimated locations of sound source 11 relative to center 21 and relative to the corresponding actual positions of sound source 11. For example, said graphical representation is generated by control unit 13.

In some embodiments, other data may be displayed in this graphical representation, such as data measured during step

1008 and representative of the orientation D of the subject's head 20 and/or of the orientation of the gaze of subject 2.

Optionally, the data may be displayed as a function of time, for example by displaying only data recorded for specific time intervals. For example, during the acquisition and measurement steps described above, the time is recorded alongside each measurement. This time recording may be performed using a digital clock associated to system 14. Said data is then displayed depending of this recorded time according to some predefined selection rule.

Figure 7:
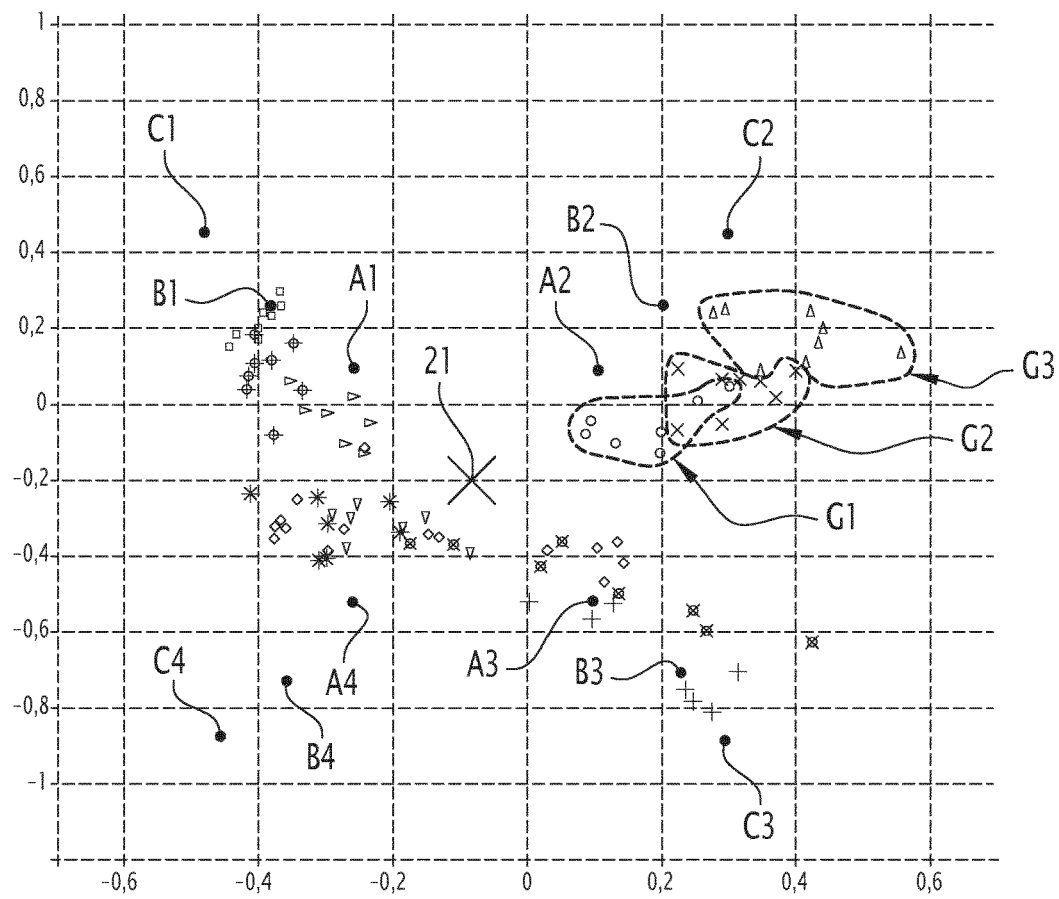
FIG. 7 is a graph illustrating an example of estimated locations of the sound source acquired by the apparatus of FIG. 1.
Figure 8:
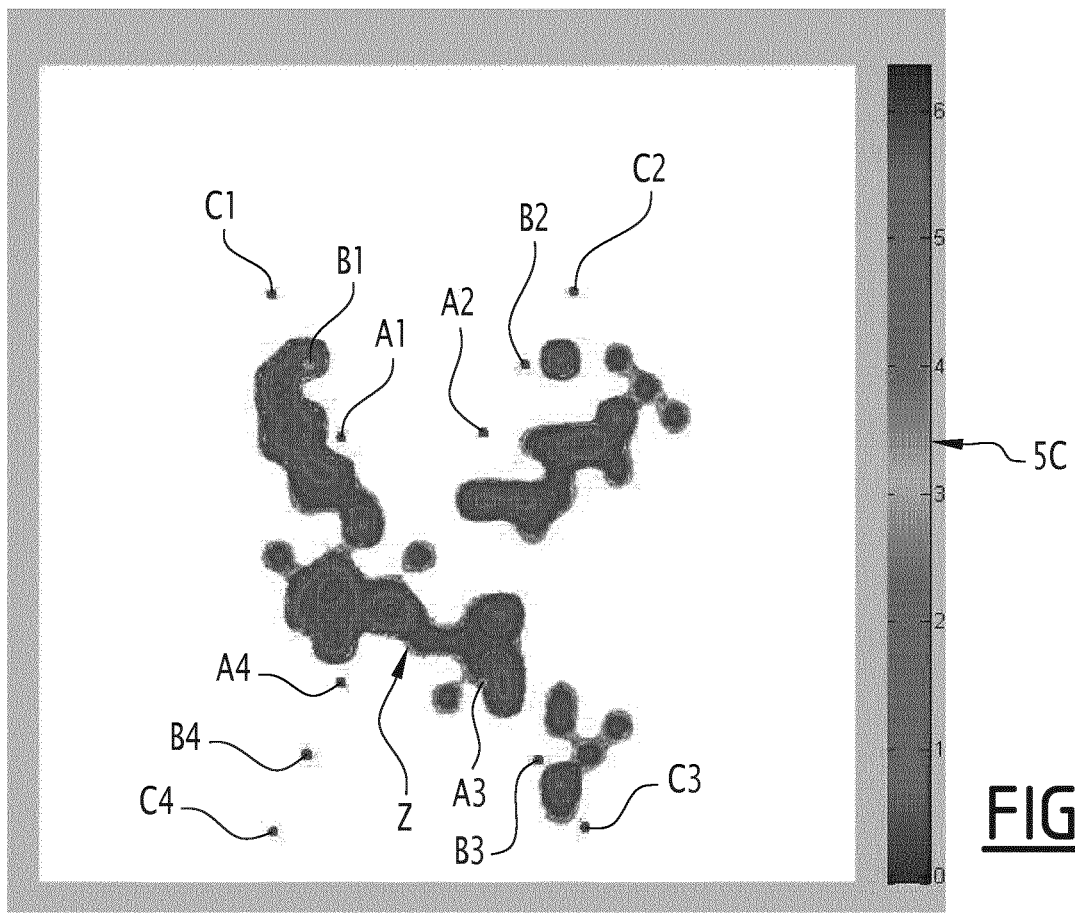
FIG. 8 is a heat map built from the acquired estimated locations of FIG. 7.

FIGS. 7 and 8 illustrate an example of collected data during a test comprising 96 test sequences, with each of the target locations A1, B1, C1, A2, B2, C2, A3, B3, C3, A4, B4 and C4 being used eight times. Therefore, there are eight estimated locations for each of the target locations A1, B1, C1, A2, B2, C2, A3, B3, C3, A4, B4 and C4. All estimated locations and target locations are here projected into the XZ plane. The origin of the scales on the abscissa and the ordinate axes of said graph is chosen arbitrarily.

On FIG. 7, the graphical representation of said acquired estimated locations is a two-dimensional data plot. Said acquired estimated locations are illustrated with a different graphical symbol for each group of acquired estimated locations associated to one of target locations A1, B1, C1, A2, B2, C2, A3, B3, C3, A4, B4 and C4. Group G1 include all data points corresponding to the estimated locations acquired during different test sequences and corresponding to predefined target location A2. The same goes with groups G2 and G3 with reference to, respectively, predefined target locations B2 and C2. Target locations A1, B1, C1, A2, B2, C2, A3, B3, C3, A4, B4 and C4 illustrated on FIG. 7 correspond to the actual position of said target locations, as measured by motion capture system 14 using optical marker 173.

In this example, acquired estimated locations corresponding to target locations A4, B4 and C4 are far from the respective actual locations of sound source 11. This may be indicative of a faulty auditory perception system of subject 2 in a specific region of space, here the region of space containing target locations A4, B4 and C4.

On FIG. 8, the graphical representation of the estimated locations of FIG. 7 is a heat map. As is known, a heat map is a two-dimensional graphical representation of data comprising a plurality of pixels where the individual intensity values of said pixels are represented as different colors, according to a predefined color scale SC. In this example, said heat map is generated by control unit 13, by defining, for each acquired estimated location of FIG. 7, a zone of several pixels having a same intensity value, such a 3×3-sized square. When two zones are superimposed with each other, the intensities of the overlapping pixels add up, changing the displayed color. On FIG. 8, reference "Z" denotes a larger zone made of several overlapping individual smaller zones each associated to an acquired estimated location. This allows a quick visualization of how acquired estimated locations are spread across space and how often they occur in a given region of space.

Optionally, during a further step 1010, control unit 13 computes, for each test sequence, the difference between the respective spatial coordinates of each estimated target location and the corresponding target location chosen for this test sequence.

If said difference is found to exceed a predefined threshold value for a predefined number of test sequences for at least one target location, then the auditory system is said to feature an abnormal condition for the region of space containing said target location.

This method may advantageously be used for therapeutic purposes, for example for generating a graphic similar to FIG. 7 or a heat map similar to FIG. 8 or a three-dimensional map as described in what follows, in order to provide data to a therapist for reeducating patients who have been implanted with hearing aids, such as hearing assistance devices, or for assessing proper functioning of said hearing aids.

Many other embodiments are possible.

For example, a three-dimensional map may be used instead of the heat-map of FIG. 8. In a possible embodiment, a graphical human-machine user interface is used to display said data on a two-dimensional video display while providing the possibility of moving and/or rotating the displayed data, so as to be able to visualize it in three dimensions.

This user interface may be implemented using graphical display hardware including a video display screen and an electronic calculator unit, such as a computer workstation or a mobile communication device. This interface is implemented by running an executable software application on said calculator unit. Said graphical display hardware includes user interface tools, such as a touchscreen and/or a mouse pointer associated to the display screen, to allow user interaction with this graphical interface.

Figure 9:
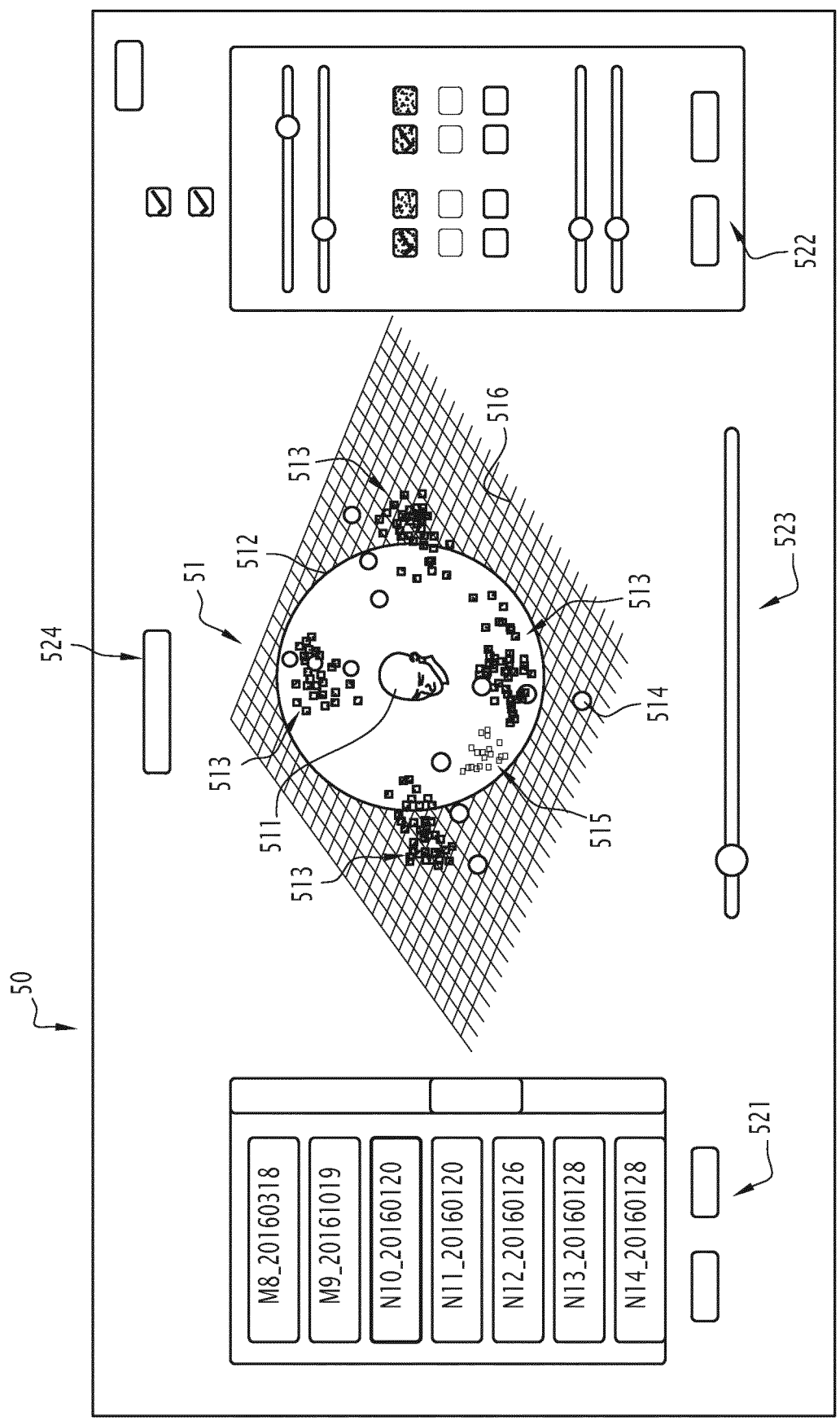
FIG. 9 is an example of a user interface screen for displaying a three-dimensional graphical representation of the acquired estimated locations of FIG. 7.

FIG. 9 illustrates an example of such an interface 50. This interface 50 comprises a central display zone 51.

The central display zone 51 comprises a center 511, here illustrated by a graphical icon of a human head. This center 511 corresponds to the position of the head of the subject 2 during the acquisition steps described above. The data points are displayed relative to this position. This zone 51 also comprises:
- a sphere 512 centered around center 511;
- icons 514 corresponding to the target locations A1, B1, C1, A2, B2, C2, A3, B3, C3, A4, B4 and C4 positioned relative to center 511, and
- a grid 516, having a regular mesh corresponding to a predefined scale. For example, one cell of the grid has a square shape having a side length equal to 0.1 meter.

Zone 51 also comprises data points 513 corresponding to the estimated locations acquired through the acquisition steps described above.

Zone 51 also comprises additional data points 515 corresponding to the measured head orientation of the subject 2 and/or to the measured gaze orientation. Said orientations are preferably displayed as data points projected on the surface of the sphere. This is easier to visualize than using arrows or the like to indicate the measured directions.

Each icon 514 can be toggled, for example by an action of the user through the interface, between an activated state and an inactive state. In an active state, the acquired data 513 and/or 515 corresponding to the target location represented by said icon 514 is displayed on the zone 51. In the inactive state, said date is not illustrated. This way, it is possible to selectively display only the acquired data relative to one or several of the target locations A1, B1, C1, A2, B2, C2, A3, B3, C3, A4, B4 and C4. In the illustrated example, all icons 514 are shown in the active state. For example, icons 514 have a different color depending whether they are in the active or inactive state, e.g. red for the active state and grey for the inactive state.

Display zone 51 can be rotated around arbitrary axes in 3D space, for example by performing by a drag-and-drop gesture using the mouse pointer interface. When zone 51 is rotated, data points 513 and/or 515, icons 514 and grid 516 are locked together with the sphere 512 and with center 511, so as to rotate together.

The interface 50 also comprises toolboxes 521, 522, 523 and 524 which are located around the central display zone 51. These toolboxes include control elements such as clickable buttons, selectors, sliders and/or menu items, for controlling the way data is displayed in the central zone 51. These items may be selectively toggled using the interface, for example using a point-and-click action on the mouse pointer or on the touchscreen interface.

As an illustrative example, toolbox 521 comprises a file browser for selecting one or several data sets among a list of acquired data sets. In the illustrated example, a data set named "N10_20160120" is selected while the other data sets are not selected.

Toolbox 522 comprises menu items such as clickable boxes and sliders for defining the size of sphere 512, the size of data points 513, 515 and/or choosing data to be displayed among the selected data set: estimated location, head orientation, gaze orientation, or any combination of said data. Toolbox 523 comprises a slide tool for varying the zoom level within zone 51. Toolbox 524 comprises selector for choosing the shape of the data points 513. Other embodiments are possible.

Figure 10:
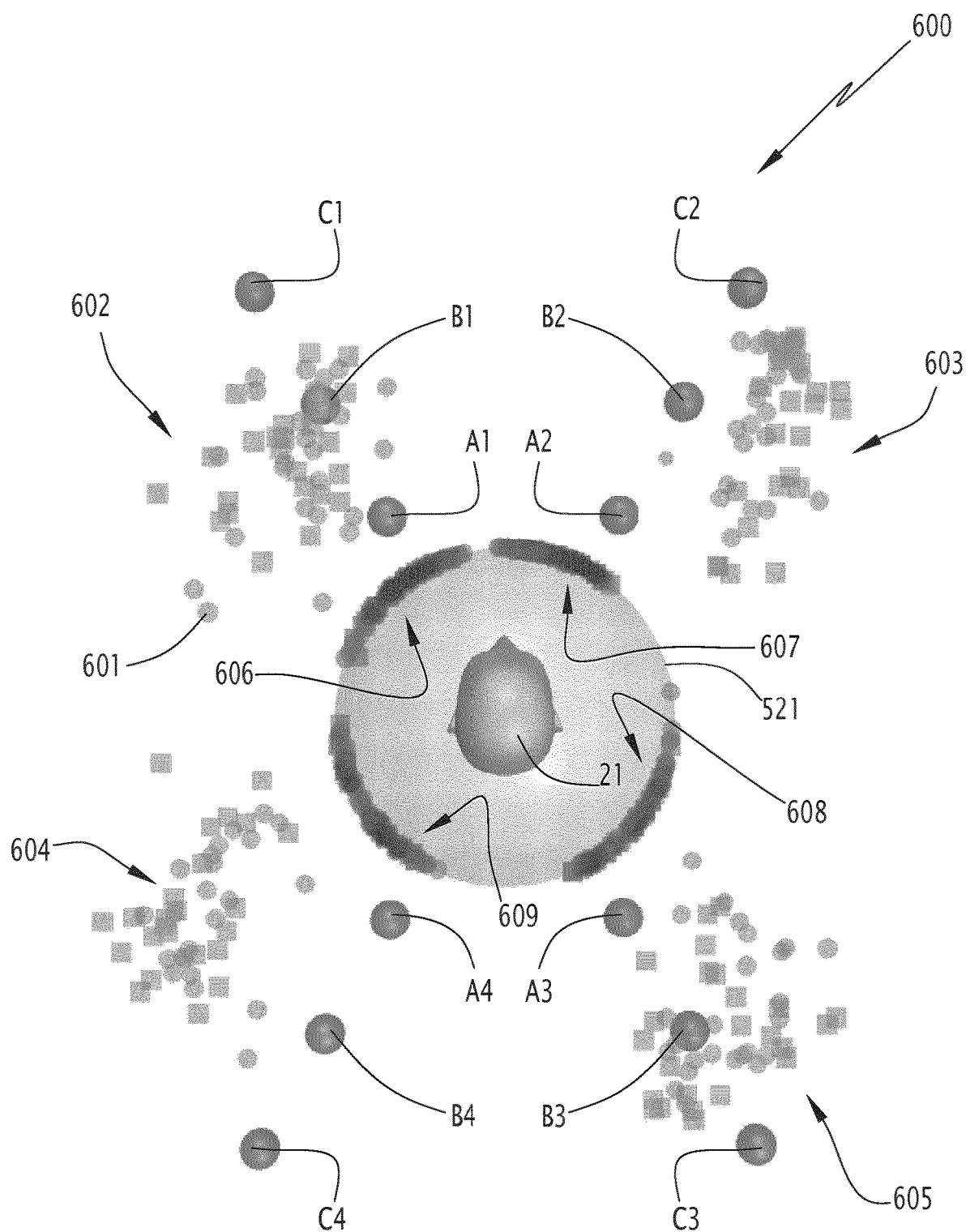
FIGS. 10 to 12 illustrate three examples of estimated locations of the sound source acquired by the apparatus of FIG. 1 and displayed on the user interface of FIG. 9.
Figure 11:
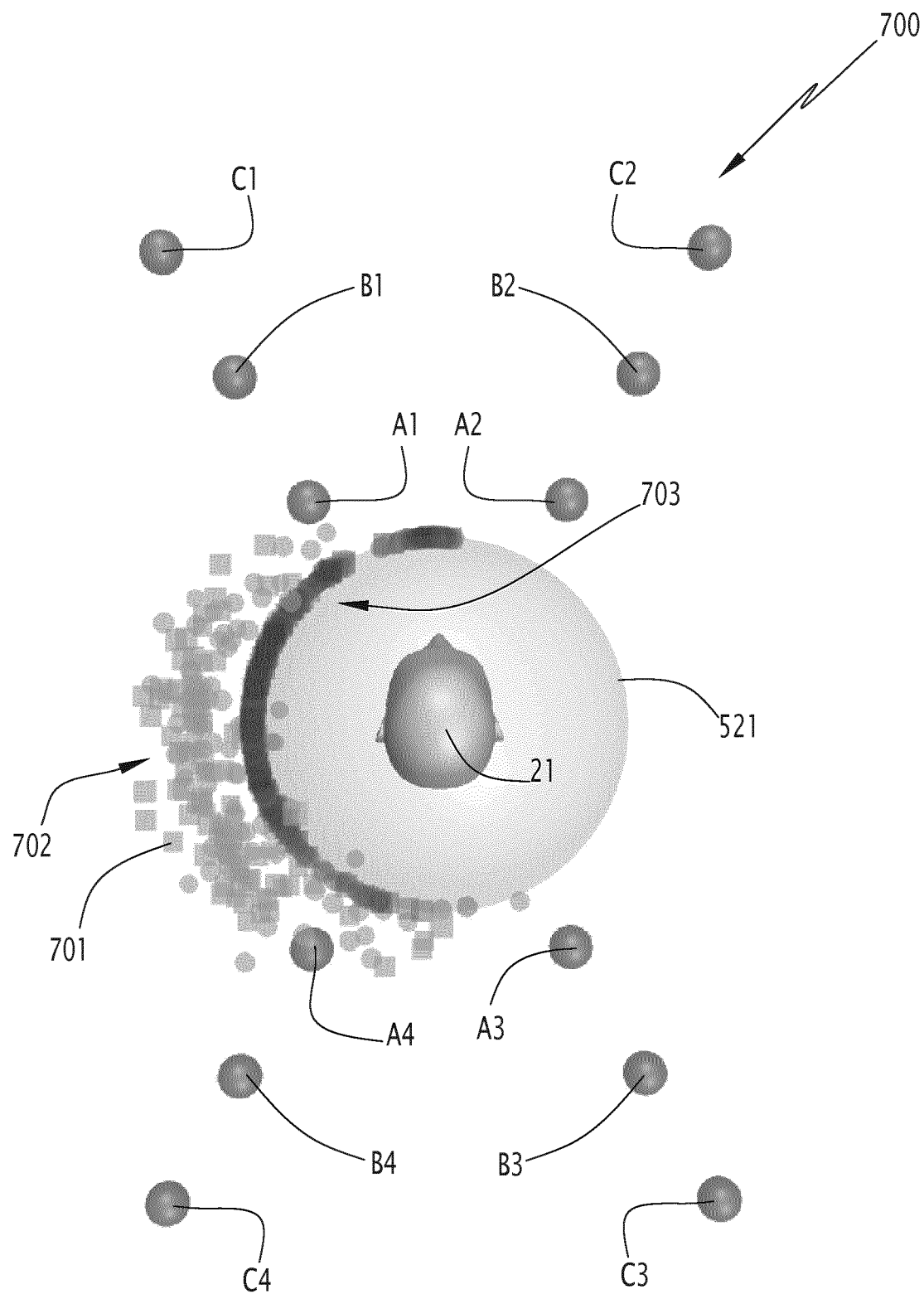
Figure 12:
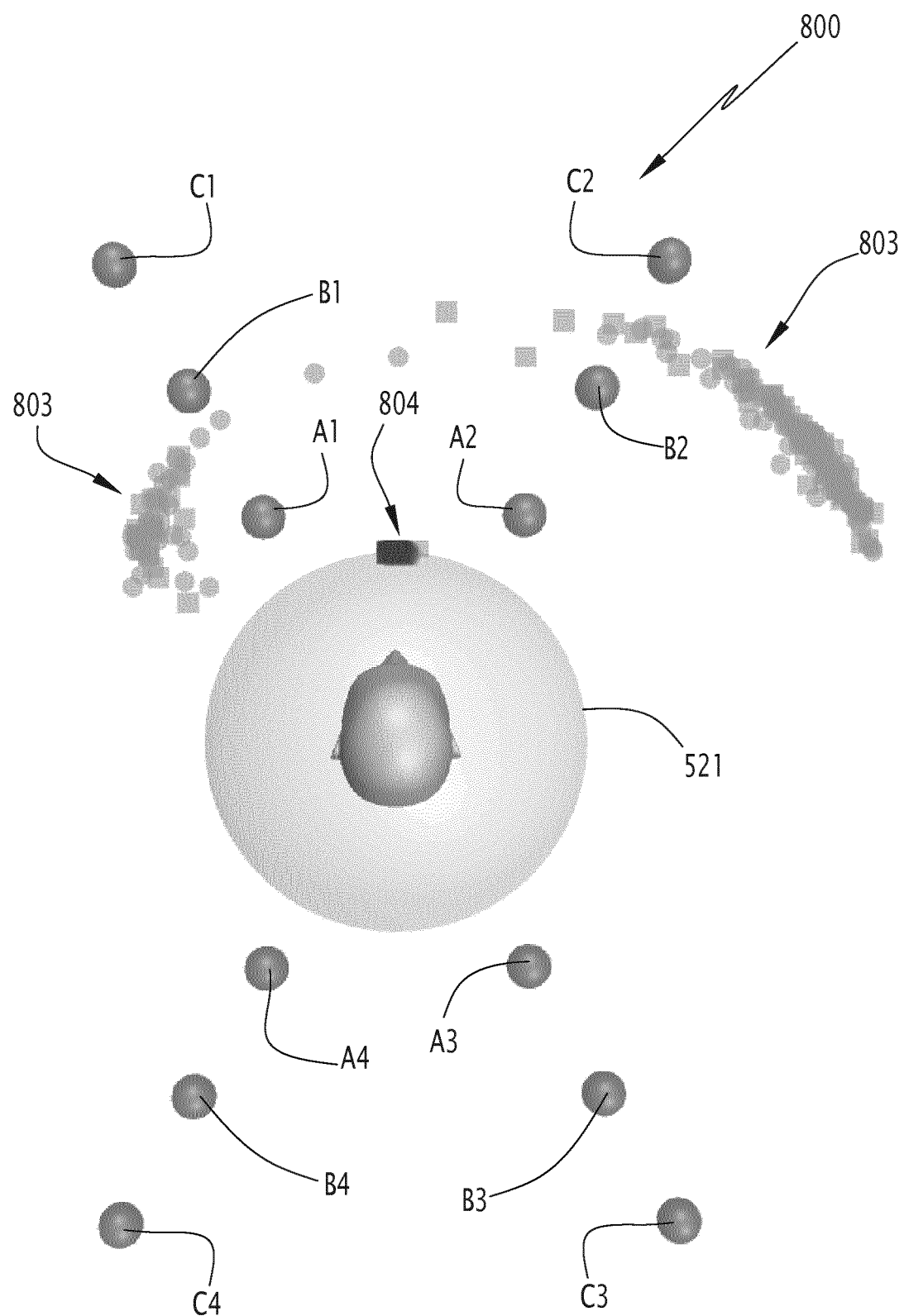

FIGS. 10 to 12 illustrate, as a comparative example, three sets of data including estimated locations of the sound source acquired by the apparatus 1 for three different subjects 2. For example, said data is displayed on user interface 50, here along a top view. In these three examples, the previously described target locations A1, B1, C1, A2, B2, C2, A3, B3, C3, A4, B4 and C4 are used.

In this example, FIG. 10 illustrates an example 600 of data collected during a test performed on a healthy subject 2 featuring normal auditory capabilities. Each data point 601 corresponds to an estimated location acquired with apparatus for this subject 2. These data points 601 are displayed relative to the head 21. In this example, data points 601 are clustered in four groups of points 602, 603, 604 and 605 which are grouped, respectively, around the four sets of target locations A1, B1, C1; A2, B2, C2; A3, B3, C3; and A4, B4, C4. This indicates that the subject 2 appears to be able to perceive and locate the sounds coming from the various directions. In addition, data relative to the head orientation and gaze orientation are projected onto the surface of sphere 512 and, in this example, are grouped along four zones 606, 607, 608 and 609, which are roughly aligned with groups 602, 603, 604 and 605. This indicates that the subject turned his/her head and eyes towards the perceived locations when the estimated locations where acquired.

FIG. 11 illustrates an example 700 of data collected during a test performed on a subject 2 with deficient auditory capabilities and being equipped with a single implant, in this case on his/her left ear. Each data point 701 corresponds to an estimated location acquired with the apparatus 1 for this subject 2. These data points 701 are displayed relative to the head 21. In this example, data points 701 are clustered on the left side of the head 21, in a single group 702 of points, which spans from the face through the back of subject 2. This indicates that the subject 2 appears to be able to perceive and locate the sounds coming from his/her left side, but that the sounds coming from the right side, i.e. on the side where no auditory implant is present, are erroneously perceived as coming from the left side. In addition, data relative to the head orientation and gaze orientation are projected onto the surface of sphere 512 and, in this example, are grouped along a single group 703 which extends roughly along group 702. This indicates that the subject turned his/her head and eyes towards the perceived locations during the acquisition steps.

FIG. 12 illustrates an example 800 of data collected during a test performed on a healthy subject 2 with deficient auditory capabilities and being equipped with an implant in each ear. Each data point 801 corresponds to an estimated location acquired with apparatus for this subject 2. These data points 801 are displayed relative to the head 21. In this example, data points 801 are clustered in two groups 802, 803 of points which are located on the forward side of patient 2, respectively on his/her left and right sides. This indicates that the subject 2 appears to be able to perceive and discriminate sounds coming either from the left or right sides, but that this subject 2 appears unable to distinguish whether the sounds are coming from a forward direction or from a back direction. In addition, data relative to the head orientation and gaze orientation are projected onto the surface of sphere 512. However, in this example, the subject 2 did not move his/her head or eyes during the acquisition steps, and thus the corresponding data points are concentrated in a single zone 804.

The embodiments and alternatives described above may be combined with each other in order to generate new embodiments of the invention.

The invention claimed is:

1. A method for acquiring a spatial map of auditory perception of a subject, wherein said method comprises a plurality of successive test sequences, each test sequence comprising:
   a) calibrating the subject's position, by displaying instructions to the subject, using a head-mounted visual display system worn by the subject, in order to acquire a reference position of the subject, the subject's position being measured using a motion capture system by measuring the spatial coordinates of a first location marker worn by the subject, said head-mounted display system preventing the subject from seeing his surroundings;
   b) choosing spatial coordinates of a target location of a real sound source, said target location being located around the subject,
   c) emitting a predefined sound, using the real sound source placed at said target location,
   d) in response to acquisition instructions generated by the subject using an acquisition interface, acquiring an estimated location of said sound source, by using the motion capture system to measure the spatial coordinates of a second location marker held and pointed by the subject towards a perceived location of the sound source, and measuring an orientation of the subject's gaze, using an eye-tracking device integrated with the head-mounted visual display system.

2. The method according to claim 1, wherein the target location of each test sequence is different from the target location of, at least, the previous test sequence.

3. The method according to claim 1, wherein the method further comprises an automatic computation of a difference between each estimated location and each corresponding target location.

4. The method according to claim 1, wherein step d) further comprises the measurement of an orientation of the subject's head, by measuring the spatial coordinates of the first location marker using the motion capture system relative to a reference position.

5. The method according to claim 1, wherein the motion capture system is a video motion capture system and the first and second markers are optical markers.

6. The method according to claim 1, wherein step a) comprises displaying positioning instructions on the head-mounted visual display.

7. The method according to claim 1, wherein, during step b), the target location is selected randomly.

8. The method according to claim 1, wherein step b) further comprises:
displaying the spatial coordinates of the target location, and
determining the actual position of the sound source, using the motion capture system to measure spatial coordinates of a third location marker placed on the sound source.

9. The method according to claim 8, wherein the motion capture system is a video motion capture system and the first, second and third markers are optical markers.

10. The method according to claim 1, wherein it further comprises generating a graphical representation of said acquired estimated locations of the sound source.

11. The method according to claim 10, wherein said graphical representation is a three-dimensional graphical representation displayed on a graphical user interface.

12. An apparatus for acquiring a spatial map of auditory perception of a subject, wherein said apparatus comprises:
a head-mounted visual display system adapted to be worn by a subject and configured for displaying instructions to the subject, said head-mounted display system preventing the subject from seeing his surroundings, the head-mounted visual display system further comprising an eye-tracking device;
a motion capture system, a first location marker and a second location marker, the motion capture system being configured for measuring the spatial coordinates of said first and second location markers,
a real sound source, configured for being placed at a target location around the subject,
an acquisition interface, configured for being commanded by the subject,
wherein said apparatus further comprises a control unit programmed to implement a plurality of successive test sequences, each test sequence comprising steps of:
a) calibrating the subject's position, by displaying instructions to the subject, using the head-mounted visual display system worn by the subject, in order to acquire a reference position of the subject, the subject's position being measured using the motion capture system by measuring the spatial coordinates of the first location marker, said first location marker being worn by the subject,
b) choosing spatial coordinates of a target location of the real sound source, said target location being located around the subject,
c) emitting a predefined sound, using said real sound source placed at said target location,
d) in response to acquisition instructions generated by the subject using the acquisition interface, acquiring an estimated location of said sound source using the motion capture system by measuring the spatial coordinates of the second location marker, said second location marker being held and pointed by the subject towards a perceived location of the sound source and a step of measurement of an orientation of the subject's gaze using the eye-tracking device.

13. The apparatus according to claim 12, wherein the control unit is further programmed, during step b), to choose spatial coordinates of a target location that is different from the target location of, at least, the previous test sequence.

14. The apparatus according to claim 12, wherein the control unit is further programmed to compute automatically a difference between each estimated location and each corresponding target location.

15. The apparatus according to claim 12, wherein the motion capture system is a video motion capture system and the first and second markers are optical markers.

* * * * *